United States Patent
Zhao et al.

(10) Patent No.: US 10,959,977 B2
(45) Date of Patent: Mar. 30, 2021

(54) APPLICATION OF PHOSPHODIESTERASE 4 INHIBITOR ZL-N-91 IN PREPARATION OF MEDICATIONS FOR LUNG CANCER PROLIFERATION AND METASTASIS

(71) Applicant: GUANGZHOU SINOGEN BIOMEDICAL TECHNOLOGY, LTD, Guangzhou (CN)

(72) Inventors: Allan Zijian Zhao, Nanjing (CN); Sijia Gong, Nanjing (CN); Yan Lin, Nanjing (CN); Fanghong Li, Nanjing (CN); Xiaoxi Li, Nanjing (CN)

(*) Notice: Subject to any disclaimer, the term of this patent is extended or adjusted under 35 U.S.C. 154(b) by 2 days.

(21) Appl. No.: 16/075,145

(22) PCT Filed: Mar. 30, 2017

(86) PCT No.: PCT/CN2017/078690
§ 371 (c)(1),
(2) Date: Aug. 3, 2018

(87) PCT Pub. No.: WO2017/133713
PCT Pub. Date: Aug. 10, 2017

(65) Prior Publication Data
US 2018/0369188 A1   Dec. 27, 2018

(30) Foreign Application Priority Data
Feb. 5, 2016 (CN) .......................... 201610081083.0

(51) Int. Cl.
| A61K 31/341 | (2006.01) |
| A61P 35/04 | (2006.01) |
| A61K 47/10 | (2017.01) |
| A61K 47/40 | (2006.01) |
| A61K 9/00 | (2006.01) |

(52) U.S. Cl.
CPC ............ *A61K 31/341* (2013.01); *A61K 47/10* (2013.01); *A61K 47/40* (2013.01); *A61P 35/04* (2018.01); *A61K 9/0019* (2013.01)

(58) Field of Classification Search
None
See application file for complete search history.

(56) References Cited

U.S. PATENT DOCUMENTS

2010/0136105 A1* 6/2010 Chen .................. A61B 17/0485
424/455

OTHER PUBLICATIONS

Pullamsetti et al. "Phosphodiesterase-4 Promotes Proliferation and Angiogenesis of Lung Cancer by Crosstalk with HIF". Oncogene. 2013; 32:1121-1134. (Year: 2013).*

Wang et al. "Zl-n-91, a Selective Phosphodiesterase 4 Inhibitor, Suppresses Inflammatory Response in a COPD-Like Rat Model". International Immunopharmacology. 2010; 10:252-258. (Year: 2010).*
Bunker A. "Poly(ethylene glycol) in Drug Delivery, Why Does it Work, and Can We Do Better?". Physics Procedia. 2012; 34:24-33. (Year: 2012).*
Loftsson et al. "Cyclodextrins in Drug Delivery". Expert Opinion on Drug Delivery. 2005; 2(2):335-351. (Year: 2005).*
Savjani et al. "Drug Solubility: Importance and Enhancement Techniques". ISRN Pharmaceutics. 2012; ID 195727, p. 1-10. (Year: 2012).*
Hall et al. "Say No to DMSO: Dimethylsulfoxide Inactivates Cisplatin, Carboplatin, and Other Platinum Complexes". Cancer Res. 2014; 74(14):3913-3922. (Year: 2014).*
Cosaertetal. "Platinum Drugs in the Treatment of Non-Small-Cell Lung Cancer". British Journal of Cancer. 2002; 87:825-833. (Year: 2002).*
Jakubowska et al. "Pulmonary Metastases of the A549-Derived Lung Adenocarcinoma Tumors Growing in Nude Mice. A Multiple Case Study". Acta Biochimica Polonica. 2013; 60(3):323-330. (Year: 2013).*
Guo et al. "FFPM, a PDE4 Inhibitor, Reverses Learning and Memory Deficits in APP/PS1 Transgenic Mice via cAMP/PKA/CREB Signalling and Anti-Inflammatory Effects". Neuropharmacology. 2017; 116:260-269 (Published Online Jan. 6, 2017). (Year: 2017).*
Sigma Aldrich [Online], "KOLLIPHOR HS 15". [Retrieved Aug. 13, 2020], Retrieved from the Internet: <URL: https://www.sigmaaldrich.com/catalog/product/sigma/42966?lang=en&region=US>. (Year: 2020).*
International Search Report in International application No. PCT/CN2017/078690, dated Jul. 3, 2017.
Tang, Huifang et al. "Action of a Novel PDE4 Inhibitor ZL-n-91 on Lipopolysa-Ccharide-Induced Acute Lung Injury", International Immunopharmacology, No. 10, Dec. 31, 2010, ISSN: 1567-5769, pp. 406-410.
Shen, Jian et al. "Phosphodiesterase-4 and Cancer", Chemistry of Life, vol. 35, No. 3, Dec. 31, 2015, pp. 350-356.

* cited by examiner

*Primary Examiner* — Leslie A. Royds Draper
(74) *Attorney, Agent, or Firm* — Jun He Law Offices P.C.; James J. Zhu; Yi Zhang

(57) ABSTRACT

The present invention discloses uses of a novel phosphodiesterase 4 (PDE4) inhibitor ZL-n-91 in preparing drugs against lung cancer proliferation and metastasis. The mouse survival curves and in vitro cell experiments show that the PDE4 inhibitor ZL-n-91 can significantly inhibit the proliferation and metastasis of lung cancer cells, indicating that this PDE4 inhibitor ZL-n-91 can become an important target for the studies on anti-lung cancer proliferation and metastasis, to provide a basis for preparing drugs against lung cancer proliferation and metastasis, with promising prospect of development and application.

5 Claims, 3 Drawing Sheets

APPLICATION OF PHOSPHODIESTERASE 4 INHIBITOR ZL-N-91 IN PREPARATION OF MEDICATIONS FOR LUNG CANCER PROLIFERATION AND METASTASIS

CROSS-REFERENCE TO RELATED APPLICATIONS

The present application is the national phase of International Application PCT/CN2017/078690, filed Mar. 30, 2017, which claims the benefit of Chinese Patent Application No. CN 201610081083.0, filed Feb. 5, 2016, the disclosure of which is incorporated herein by reference in the entirety.

FIELD OF THE INVENTION

The present invention relates to uses of a PDE4 inhibitor, and in particular to uses of a PDE4 inhibitor ZL-n-91. It belongs to the field of tumor biology.

BACKGROUND

Cancer is an important cause of human death, and lung cancer is one of the malignant tumors with the fastest increase in morbidity and mortality and the greatest threat to human health and life. Globally, lung cancer is the second most common cancer in males. In 2012, almost 1.6 million people died of lung cancer in the world, and the number of such cases accounted for more than one-third. Lung cancer has the highest incidence in males in china, and 80%-85% of them are non-small cell lung cancer (NSCLC). Conventional therapies for lung cancer include topical treatment (including surgery, radiation therapy, etc.) and systemic treatment (including conventional chemotherapy, molecularly targeted drug therapy, etc.). Although great progress has been made in modern medical researches and some progress in the radiotherapy, chemotherapy, and surgical treatment have been achieved for lung cancer, the overall prognosis of lung cancer is still poor, and its 5-year survival rate is less than 15%. Therefore, looking for new method for treating lung cancer has become an issue urgently to be solved by scientists.

Phosphodiesterases (PDEs) have the function of hydrolyzing intracellular second messenger cAMP or cGMP, to affect the second messenger-mediated signaling pathways and regulate cell functions. PDEs include 11 subtypes, of which, PDE4 specifically hydrolyzes cAMP. PDE4 is mainly expressed in a variety of inflammatory cells, including mast cells, macrophages, lymphocytes, epithelial cells, etc. PDE4 is involved in related physiological and pathological processes such as promoting activation of monocytes and macrophages, neutrophil infiltration, proliferation of vascular smooth muscle, vasodilation and myocardial contraction, etc., having influence on central nervous system functions, cardiovascular functions, inflammation/immune system, and cell adhesion, etc. Studies have shown that PDE4 inhibitors (PDE4i) have effects of anti-inflammation, anti-allergy and anti-platelet activation. Its specific mechanisms include the following: 1) inhibiting the release of a variety of inflammatory mediators/cytokines and inhibiting the expression of IL-4 and IL-5 genes; 2) inhibiting leukocyte activation (e.g., respiratory burst) and inhibiting leukocyte migration; 3) inhibiting the expression or upregulation of cell adhesion factor (CAM); 4) inducing the production of cytokines with inhibitory activity, such as IL-6; 5) inducing apoptosis; 6) stimulating the release of endogenous hormones and catecholamines.

At present, PDE4 inhibitors that have been developed or being developed mainly target on chronic obstructive pulmonary disease (COPD), asthma, inflammatory bowel disease, arthritis, etc. However, many studies have shown that PDE4 inhibitors have a significant inhibitory effect on malignant tumors. Patricia Goldhoff xenografted human glioblastoma U87 cells in nude mice and used PDE4 inhibitors to prolong the survival time of tumor-bearing mice. In 2006, Motoshi Narita found that PDE4i could inhibit the growth of human melanoma cells. Petros X. E. Mouratidis found that, after adding PDE4 inhibitors CC-8075 and CC-8062 to pancreatic cancer cells, cell proliferation was decreased and cell apoptosis increased.

The existing PDE4 inhibitors mainly include Rolipram, Cilomitast, Roflumilast, etc. Since Rolipram and Cilomitast may induce dizziness, headache and nausea, vomiting and other gastrointestinal adverse reactions, the application of these drugs are limited in clinical practices. One of the possible causes of adverse reactions in the gastrointestinal tract is the poor specificity of PDE4 inhibitors, which moderately and selectively inhibits the entire PDE family. For example, Cilomitast inhibits PDE4 with Ki of 92 nM, only 500 to 1000 times of Ki for PDE1, 2, 3, and 5. Therefore, a high dose of Cilomilast can interact with other PDE family members and cause side effects. In fact, most PDE4 inhibitors have a common side effect of vomiting at high doses. Although Roflumilast has been approved by the US FDA for the treatment of COPD with its effect of reducing lung inflammation, resisting oxidative stress, effectively relieving pulmonary fibrosis, enhancing mucosal clearance and remodeling the airway, it has caused adverse reactions such as diarrhea, weight loss, nausea, atrial fibrillation and aggravated mental illness (such as insomnia, anxiety, depression), etc.

SUMMARY

The object of the present invention is to provide uses of PDE4 inhibitor ZL-n-91 in preparing drugs against lung cancer proliferation and metastasis.

In order to achieve the object, the present invention adopts the following technical solutions.

The use of PDE4 inhibitor ZL-n-91 in preparing drugs against lung cancer proliferation is within the scope of protection of the present invention.

The present invention studies the pathophysiological effects of ZL-n-91 using C57BL6 wild-type mice that are injected with mouse lung cancer LLC by tail vein injection as models and A549 subcutaneous tumor models. Experiments have confirmed that this inhibitor can significantly inhibit the proliferation of lung cancer cells, laying a foundation for the studies of preparing drugs against lung cancer proliferation.

The use of PDE4 inhibitor ZL-n-91 in preparing drugs against lung cancer metastasis is also within the scope of protection of the present invention.

The present invention studies the biological effects of ZL-n-91 using mouse lung cancer cell LLC and human lung cancer cell A549. Experiments have confirmed that this inhibitor can significantly inhibit the metastasis of lung cancer cells, laying a foundation for the studies of preparing drugs against lung cancer metastasis.

The use of PDE4 inhibitor ZL-n-91 in preparing drugs against lung cancer proliferation and metastasis is also within the scope of protection of the present invention.

For the foregoing uses, preferably, drugs are administered orally, by injection and in nebulized form.

The PDE4 inhibitor ZL-n-91 of the present invention has the following formula:

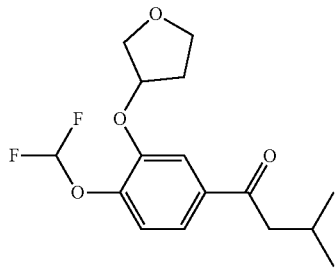 [SMILES: CC(C)CC(=O)c1ccc(OC(F)F)c(OC2CCOC2)c1]

The PDE4 inhibitor ZL-n-91 of the present invention can be directly purchased or synthesized by self, for example, it can be synthesized and prepared with reference to [Ruihong Ma, Bin-yan Yang, Chang-you Wu. A selective PDE4 (PDE4) inhibitor Zl-n-91 suppresses IL-17 production by human memory Th17 cells. International Immunopharmacology, 2008, 8(10):1408-1417.].

In order to demonstrate the effect of the compound in the present invention, the role of PDE inhibitor ZL-n-91 in treating lung cancer proliferation and metastasis is further described in the following embodiments in combination with in vivo survival curve test and in vitro test of mice and the test results.

The present invention can achieve the following beneficial effects. The PDE4 inhibitor ZL-n-91 of the present invention can significantly inhibit the proliferation and metastasis of lung cancer cells, indicating that this PDE4 inhibitor ZL-n-91 is expected to become an important target for the studies on anti-lung cancer proliferation and metastasis, to provide a basis for preparing drugs against lung cancer proliferation and metastasis, with promising prospect of development and applications. The intensity of ZL-n-91 on PDE4D is more than 5,000 times that of other PDE family members. Compared with other PDE4 inhibitors, this compound has a higher selectivity for PDE4D. It is highly targeted and produces small side effects, and can effectively reduce or even avoid adverse reactions such as vomiting.

BRIEF DESCRIPTION OF THE FIGURES

FIG. 1 shows the proliferation of mouse lung cancer cell LLC at 24 hours after administration of different doses of ZL-n-91.

FIG. 2 on the left and right show the proliferation of human lung cancer cell A549 at 24 hours and 48 hours after administration of different doses of ZL-n-91.

FIG. 3 shows the migration of mouse lung cancer cell LLC at 24 hours after administration of different doses of ZL-n-91.

FIG. 4A represents the normal group, FIG. 4B represents the solvent group, and FIG. 4C represents the high-dose group, and FIG. 4D represents the low-dose group.

DETAILED DESCRIPTION

Figure 4:
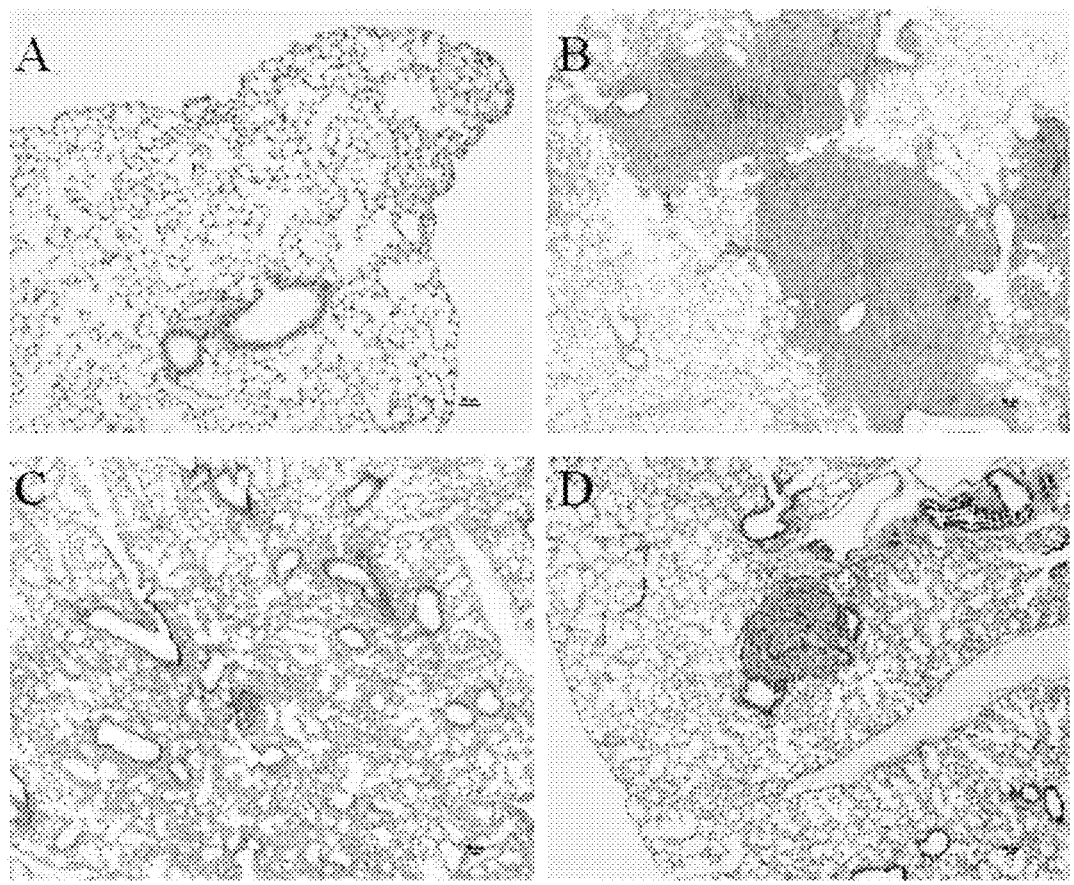
FIG. 4 shows pathological sections by H&E staining of lung tissues from mice inoculated with $5 \times 10^5$ mouse lung cancer cells (LLC) at 3 weeks after administration of different doses of ZL-n-91.

The present invention will be better understood based on the following embodiments. However, it is easily understood by those skilled in the art that the contents described in the embodiments are only for illustrating the present invention, and should not and do not limit the present invention described in detail in the claims.

Example 1: Effect of ZL-n-91 on Proliferation of Lung Cancer Cells Detected by CCK8 Method 1) Take cells in the logarithmic growth phase (A549 and LLC, respectively) to prepare single-cell suspensions. Plate cell suspensions to 96-well plates at 100 ul/well (containing $1 \times 10^4$ cells) and divide them into 5 groups: blank control group, DMSO group, 10 uM group, 50 uM group, 100 uM group, 200 uM group. Each group includes 6 replicates. Pre-incubate cells for 24 hours (at 37° C., 5% $CO_2$);

2) Use the fresh medium, add different concentrations of ZL-n-91 to each group, continue to culture cells for 24 hours and 48 hours respectively (at 37° C., 5% $CO_2$);

3) Add 100 ul of 10% CCK-8 solution to each well and avoid air bubbles;

4) Continue to incubate cells for 1-2 hours, take out the culture plate at 30 min, 60 min and 90 min respectively, and then determine the absorbance at 450 nm using a microplate reader.

Figures 1, 2, 3:
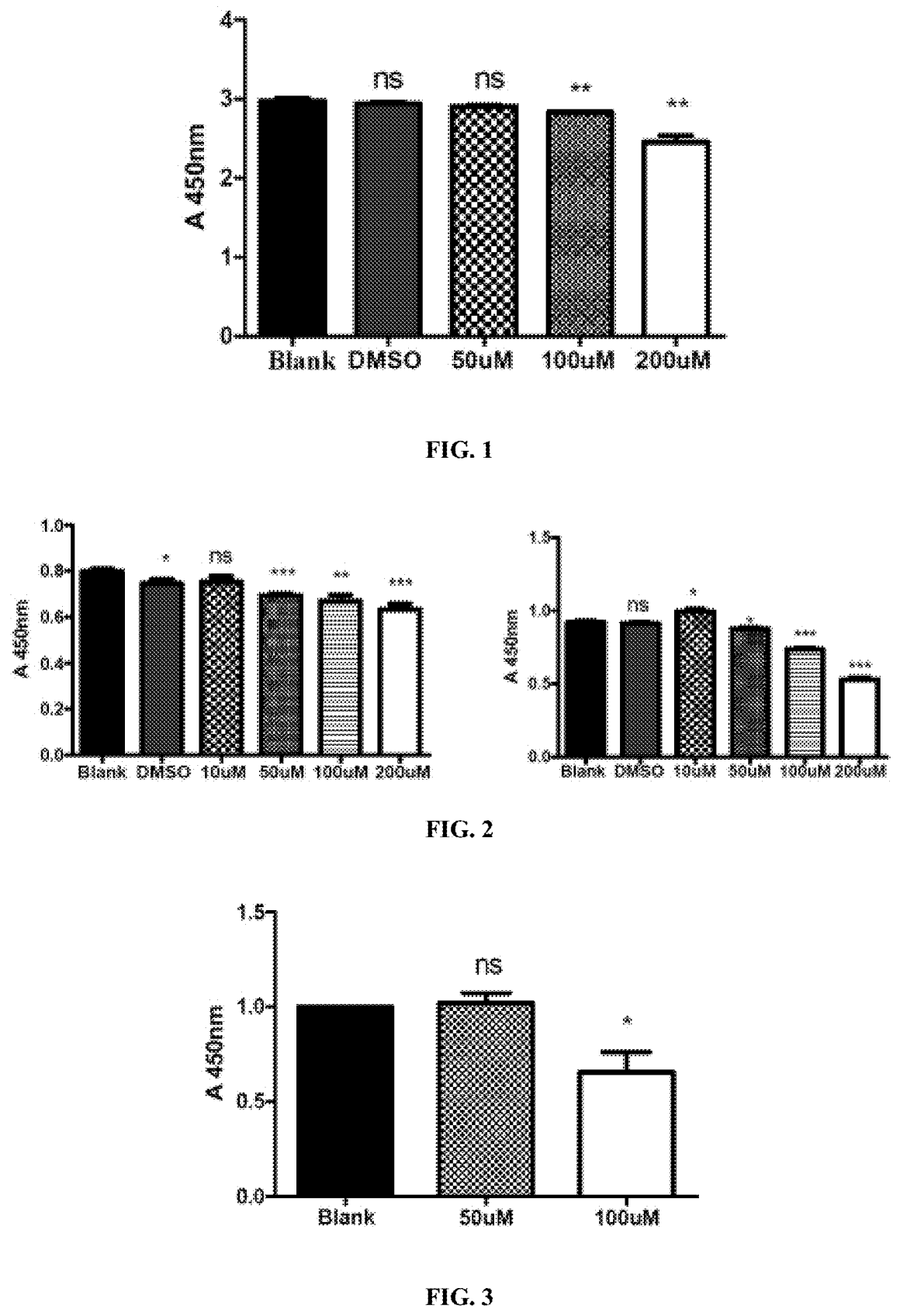

The results are shown in FIG. 1 and FIG. 2. With increased ZL-n-91 concentration, the proliferation of mouse lung cancer LLC and human lung cancer cell A549 significantly decreased.

Example 2: Effect of ZL-n-91 on Migration of Mouse Lung Cancer Cells (LLC)

1) Take cells at logarithmic growth phase to prepare a suspension with serum-free DMEM medium. Add 100 ul cell suspension/well (containing $5 \times 10^4$ cells) to the upper transwell chambers and divide them into 3 groups: blank control group, 50 uM group, 100 uM group. Each group includes 3 replicates. Treat cells with different concentrations of drugs;

2) Add complete DMEM medium with 10% FBS to the lower chamber of the 12-well plate;

3) 24 hours later, take out the upper chambers, place to iced methanol for fixation for 30 min, and then naturally dry it at a room temperature;

4) Add 600 ul of 0.1% crystal violet solution to a 12-well plate to stain the cells in the lower surface of the chamber for 15 min;

5) Add PBS, and after 5 min, pipette the PBS and gently wipe off the cells in the upper chamber with a clean cotton swab. Wash 3 times with PBS. Dry naturally at room temperature;

6) Add 300 ul of 10% acetic acid solution to a 12-well plate to soak the lower surface of the chamber for 10 min, to dissolve the crystal violet in the cells;

7) Add 100 ul solution to a 96-well plate, and determine the absorbance at 570 nm using a microplate reader.

The results (FIG. 3) showed that, when the drug concentration was 100 uM, ZL-n-91 significantly inhibited the migration of mouse lung cancer cells (LLC).

Example 3: Effect of ZL-n-91 on Mice with Lung Cancer

1) Culture lung cancer cells (LLC) in an incubator at 5% $CO_2$, 37° C., saturated humidity. Collect cells that grow well in the logarithmic phase, dilute them with 1×PBS, and adjust the concentration to $1.67 \times 10^6$/ml;

2) Inoculate 0.3 ml of prepared cell suspension to wild-type C57BL6 mice via tail veins using a 1 ml sterile syringe;

3) Mice receive drug treatment at 3 days after inoculation.

4) Solvent preparation: 40% hydroxypropyl-β-cyclodextrin and 6% polyglycol stearate 15 in physiological saline;

5) Take 10 mg, 20 mg, 40 mg of ZL-n-91 and dissolve in the above solvent, mix well by vortexing, to prepare three doses of 5 mg/kg, 10 mg/kg and 20 mg/kg;

6) Daily intragastric administration of 100 ul of the solvent and the above three concentrations of drugs respectively. Observe and record the survival of mice, and draw the survival curve of mice.

7) Sacrifice some mice at 3 weeks after administration of the drug and then perform pathological analysis with paraffin-embedded tissue sections.

Figure 5:
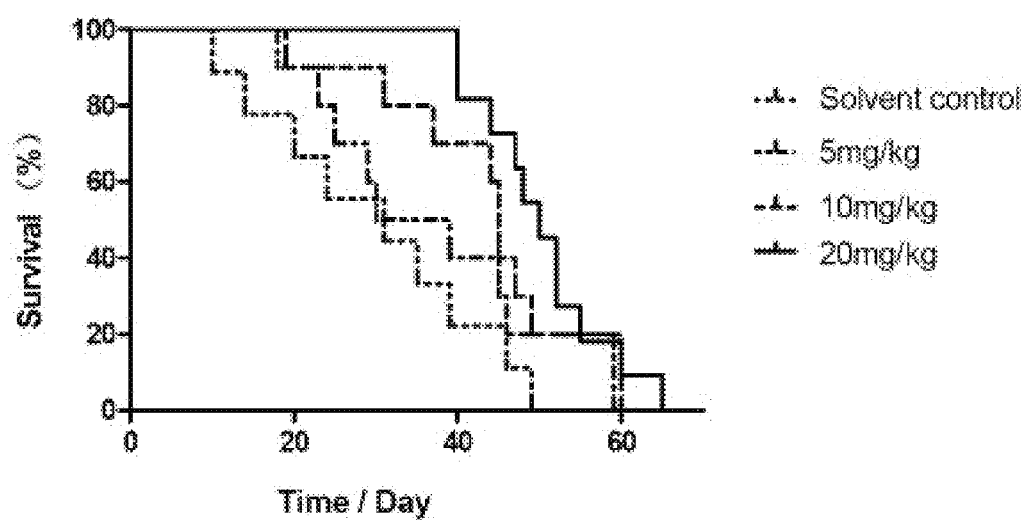
FIG. 5 shows the survival curve of mice inoculated with $5 \times 10^5$ mouse lung cancer cells (LLC) after administration of different doses of ZL-n-91.

Results are shown in FIG. 4. Massive infiltration of lung lobe by malignant tumor cells occurs in the mice of the control group. With the increase of the administration dose, the tumor cell aggregation of the mice is alleviated, and the tumor area of the high-dose mice is significantly smaller than that of the control group. FIG. 5 showed that, after different doses of ZL-n-91 were given to mice with lung cancer, the survival time of mice is significantly prolonged with the increase in drug dose, indicating that ZL-n-91 significantly prolongs the survival time of mice with lung cancer.

Example 4: Treatment of Nude Mice Subcutaneously Implanted with A549 Cells

1) Take A549 cells in logarithmic growth phase to prepare a single-cell suspension with serum-free F-12K medium, and dispense 120 ul aliquots per 1.5 ml EP tubes (containing $2 \times 10^6$ cells);

2) Inoculate 0.1 ml of prepared cell suspension subcutaneously into nude mice using 1 ml sterile syringe;

3) Treat the mice with drug at 3 days after inoculation.

4) Divide nude mice into two groups: solvent control group and administration group (10 mg/kg). Mice receive medication every day. Measure the subcutaneous tumor volume of the nude mice twice a week;

5) When the mouse tumor volume reaches 1500 $mm^3$, take out the mouse tumor, compare the tumor size, and record the tumor weight.

Figure 6:
FIG. 6 shows the change of tumor volume and tumor size in mice with xenograft of human lung cancer cell A549 subcutaneously after administration of different doses of ZL-n-91.
Figure 7:
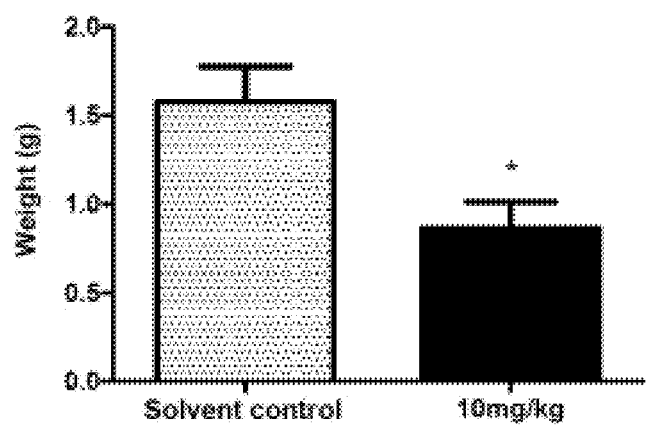
FIG. 7 shows the change of tumor weight in mice with human lung cancer cell A549 subcutaneous xenograft after administration of different doses of ZL-n-91.

The results are shown in FIG. 6 and FIG. 7. After medication, the tumor volume and weight were about ⅓ of those of the control group, indicating that ZL-n-91 has significant inhibitory effect on the growth of A549 subcutaneous xenograft.

The above experiments show that the PDE4 inhibitor ZL-n-91 used in the present invention can not only inhibit the proliferation of cancer cells, but also inhibit the metastasis of cancer cells, presenting a good anti-tumor effect.

What is claimed is:

1. A method for treating lung cancer in a subject in need thereof, comprising administering a phosphodiesterase 4 (PDE4) inhibitor to the subject, wherein the PDE4 inhibitor is ZL-n-91, and wherein the PDE4 inhibitor is dissolved in a solvent comprising 40% hydroxypropyl-β-cyclodextrin and 6% polyglycol stearate 15.

2. The method according to claim 1, wherein the lung cancer is metastatic.

3. The method according to claim 1, wherein the PDE4 inhibitor is administered orally, by injection or in nebulized form.

4. The method according to claim 1, wherein the PDE4 inhibitor is administered to the subject at a concentration of 5 mg/kg, 10 mg/kg, or 20 mg/kg.

5. The method according to claim 1, wherein the solvent further comprises physiological saline.

* * * * *

UNITED STATES PATENT AND TRADEMARK OFFICE
CERTIFICATE OF CORRECTION

| | |
|---|---|
| PATENT NO. | : 10,959,977 B2 |
| APPLICATION NO. | : 16/075145 |
| DATED | : March 30, 2021 |
| INVENTOR(S) | : Allan Zijian Zhao et al. |

It is certified that error appears in the above-identified patent and that said Letters Patent is hereby corrected as shown below:

On the Title Page

Item (71) Applicant:
Correct the name of the applicant to "GUANGZHOU HUAZHEN PHARMACEUTICAL CO., LTD."

Signed and Sealed this
Eleventh Day of April, 2023

Katherine Kelly Vidal
*Director of the United States Patent and Trademark Office*